United States Patent
Sasaki et al.

(10) Patent No.: US 11,160,674 B2
(45) Date of Patent: Nov. 2, 2021

(54) HIGH PERFORMANCE BIOABSORBABLE STENT

(71) Applicants: Japan Medical Device Technology Co., LTD., Kumamoto (JP); FUJI LIGHT METAL CO., LTD., Kumamoto (JP)

(72) Inventors: Makoto Sasaki, Kumamoto (JP); Yuki Koga, Kumamoto (JP); Yuki Okazawa, Kumamoto (JP); Hironori Ueda, Kumamoto (JP); Masashi Inoue, Kumamoto (JP)

(73) Assignees: Japan Medical Device Technology Co., LTD., Kumamoto (JP); FUJI LIGHT METAL CO., LTD., Kumamoto (JP)

( * ) Notice: Subject to any disclaimer, the term of this patent is extended or adjusted under 35 U.S.C. 154(b) by 91 days.

(21) Appl. No.: 16/523,645

(22) Filed: Jul. 26, 2019

(65) Prior Publication Data
US 2019/0343666 A1    Nov. 14, 2019

Related U.S. Application Data

(63) Continuation of application No. PCT/JP2018/002753, filed on Jan. 29, 2018.

(30) Foreign Application Priority Data

Jan. 30, 2017  (JP) .............................. JP2017-014668

(51) Int. Cl.
*A61L 31/02*  (2006.01)
*A61L 31/14*  (2006.01)
(Continued)

(52) U.S. Cl.
CPC .............. *A61F 2/90* (2013.01); *A61L 31/022* (2013.01); *A61L 31/148* (2013.01); *A61F 2/958* (2013.01);
(Continued)

(58) Field of Classification Search
CPC .......................................... A61F 2310/00041
See application file for complete search history.

(56) References Cited

U.S. PATENT DOCUMENTS

| 5,342,576 A | 8/1994 | Whitehead |
| 6,080,177 A | 6/2000 | Igaki et al. |

(Continued)

FOREIGN PATENT DOCUMENTS

| CN | 101257860 A | 9/2008 |
| CN | 101468216 A | 7/2009 |

(Continued)

OTHER PUBLICATIONS

Extended European Search Report for European Application No. 18744765.1 dated Aug. 28, 2020, (11 pages).

(Continued)

*Primary Examiner* — Jacqueline Woznicki
(74) *Attorney, Agent, or Firm* — Kagan Binder, PLLC

(57) ABSTRACT

To provide a stent excellent in deformability, capable of maintaining a radial force for a longer period of time, and having bioabsorbability and a method of producing the same. The bioabsorbable stent has a core structure including a magnesium alloy and a corrosion resistant layer on the core structure, wherein the core structure is formed from a magnesium alloy containing 90 mass % or more of Mg as a main component, Zn, Zr, and Mn as accessory components, and 30 ppm or less of unavoidable impurities selected from the group consisting of Fe, Ni, Co, and Cu, and the alloy excluding aluminum and at least one sort of rare earths (Continued)

selected from the group consisting of Sc, Y, Dy, Sm, Ce, Gd, and La; and the corrosion resistant layer containing magnesium fluoride as a main component with a hydrophilic smooth surface is formed on the core structure with a smooth surface.

10 Claims, 9 Drawing Sheets

(51) Int. Cl.
| | |
|---|---|
| *A61L 31/06* | (2006.01) |
| *A61L 31/10* | (2006.01) |
| *A61L 31/16* | (2006.01) |
| *A61F 2/90* | (2013.01) |
| *A61F 2/958* | (2013.01) |

(52) U.S. Cl.
CPC ............ *A61F 2210/0004* (2013.01); *A61F 2310/00011* (2013.01); *A61F 2310/00041* (2013.01); *A61F 2310/00425* (2013.01); *A61L 31/06* (2013.01); *A61L 31/10* (2013.01); *A61L 31/16* (2013.01); *A61L 2420/00* (2013.01)

(56) References Cited

U.S. PATENT DOCUMENTS

| | | | |
|---|---|---|---|
| 8,569,333 B2 | 10/2013 | Mollison et al. | |
| 9,474,637 B2 | 10/2016 | Zhao | |
| 9,480,550 B2* | 11/2016 | Yamauchi | A61F 2/82 |
| 9,522,220 B2 | 12/2016 | Edick | |
| 9,593,397 B2* | 3/2017 | Imwinkelried | C22C 23/02 |
| 10,052,405 B2 | 8/2018 | Koo et al. | |
| 10,350,093 B2 | 7/2019 | Yan et al. | |
| 2002/0004060 A1* | 1/2002 | Heublein | A61B 17/1204 424/422 |
| 2007/0135908 A1 | 6/2007 | Zhao | |
| 2008/0071358 A1* | 3/2008 | Weber | A61F 2/82 623/1.42 |
| 2009/0131540 A1 | 5/2009 | Hiromoto et al. | |
| 2010/0145436 A1 | 6/2010 | Weber et al. | |
| 2010/0305684 A1 | 12/2010 | Kim et al. | |
| 2013/0004362 A1* | 1/2013 | Soba | A61L 31/14 420/417 |
| 2013/0209195 A1 | 8/2013 | Kuwabara et al. | |
| 2014/0200652 A1 | 7/2014 | Bayer et al. | |
| 2015/0196691 A1 | 7/2015 | Covelli et al. | |
| 2016/0022876 A1 | 1/2016 | Imwinkelried et al. | |
| 2016/0129162 A1 | 5/2016 | Pulugurtha et al. | |
| 2018/0264180 A1* | 9/2018 | Sasaki | A61L 31/16 |
| 2021/0001013 A1 | 1/2021 | Sasaki et al. | |

FOREIGN PATENT DOCUMENTS

| | | |
|---|---|---|
| CN | 101629260 A | 1/2010 |
| CN | 102548589 A | 7/2012 |
| CN | 104046867 A | 9/2014 |
| CN | 104498790 A | 4/2015 |
| CN | 104630587 A | 5/2015 |
| CN | 105256213 A | 1/2016 |
| EP | 0482947 A1 | 4/1992 |
| GB | 851871 A | 10/1960 |
| JP | 3518704 B1 | 12/1960 |
| JP | 2842943 B2 | 1/1999 |
| JP | 2004183062 A | 7/2004 |
| JP | 2006087704 A | 4/2006 |
| JP | 2009530039 A | 8/2009 |
| JP | 2010013725 A | 1/2010 |
| JP | 2010503486 A | 2/2010 |
| JP | 2012082474 A | 4/2012 |
| JP | 2013215332 A | 10/2013 |
| JP | 5425364 B2 | 2/2014 |
| JP | 5701497 B2 | 4/2015 |
| JP | 2017501756 A | 1/2017 |
| WO | 2007108450 A1 | 9/2007 |
| WO | 2007112006 A2 | 10/2007 |
| WO | 2008036554 A2 | 3/2008 |

OTHER PUBLICATIONS

Gui et al., "Mechanical and corrosion properties of Mg—Gd—Zn—Zr—Mn biodegradable alloy by hot extrusion", Journal of Alloys and Compounds, vol. 685, ISSN: 0925-8388, pp. 222-230, (2016), (9 pages).
E-Space English Abstract for CN104498790A.
E-Space English Abstract for JP2006087704A.
Database Compendex (Online), "Microstructure and properties of Mg—3Zn—0.8Zr—xMn alloy", Database accession No. E20151300692382, Engineering Information, Inc., New York, NY, US, vol. 36, No. 2, pp. 27-31, Feb. 25, 2015, (1 page).
Agarwal et al., "Biodegradable magnesium alloys for orthopaedic applications: A review on corrosion, biocompatibility and surface modifications", Materials Science and Engineering: C, vol. 68, pp. 948-963, 2016, (16 pages).
E-Space English Abstract for CN101629260A.
E-Space English Abstract for CN104046867A.
E-Space English Abstract for CN104630587A.
E-Space English Abstract for CN105256213A.
E-Space English Abstract for JP3518704B1.
E-Space English Abstract for JP2004183062A.
E-Space English Abstract for JP2010013725A.
E-Space English Abstract for JP2012082474A.
E-Space English Abstract for WO2007108450A1.
International Preliminary Report on Patentability and English Translation thereof for International Application No. PCT/JP2018/002753, dated Aug. 8, 2019 (13 pages).
Mao, L. et al., "Enhanced bioactivity of Mg—Nd—Zn—Zr alloy achieved with nanoscale MgF2 surface for vascular stent application", ACS Appl Mater Interfaces, 2015, vol. 7, No. 9, pp. 5320-5330, abstract, p. 5320, right column, line 2 from the bottom to p. 5321, left column, line 2, section of "Materials and surface modification", (11 Pages).
Yamamoto, A., "Biomedical application of magnesium alloys", Journal of Japan Institute of Light Metals, 2008, vol. 58, No. 11, pp. 570-576, section of "1. Introduction", p. 674, lines 14-19 with machine English translation, (6 pages).
Maeda, T. et al., "Fabrication and mechanical properties of biodegradable magnesium stent", Journal of Japan Institute of Light Metals, Jun. 2016, vol. 66, No. 6, pp. 312-317, section of "1. Introduction", section of "2. Creation of magnesium alloy for biodegradable stent" including English abstract, (6 pages).
English Abstract for JP2010-503486A.
English Abstract for JP2009-530039A.
English Abstract for JP2842943B2.
English Abstract for JP2013-215332A.
English Abstract for JP5425364B2.
English Abstract for JP5701497B2.
Notice of Reasons for Refusal for Japanese Application No. 2018-564686 dated Oct. 8, 2019, (6 pages).
First Examination Report, and English Translation thereof, for corresponding Indian Patent Application No. 201917028971, dated Mar. 22, 2021, (6 pages).
First Chinese Office Action, and English Machine Translation thereof, for corresponding Chinese Patent Application No. 201880009024.X, dated Apr. 6, 2021, (9 pages).
E-Space English Abstract for CN101257860A.
E-Space English Abstract for CN101468216A.
E-Space English Abstract for CN102548589A.

* cited by examiner

MgF$_2$ LAYER SURFACE 28 WITH MIRROR SURFACE

Mg ALLOY SURFACE 29 WITHOUT MIRROR SURFACE

COATING 30 ON MgF$_2$ LAYER SURFACE WITH MIRROR SURFACE

COATING 31 ON Mg ALLOY SURFACE WITH MIRROR SURFACE

HIGH PERFORMANCE BIOABSORBABLE STENT

CROSS REFERENCE TO THE RELATED APPLICATION

This application is a continuation application, under 35 U.S.C. § 111(a), of international application No. PCT/JP2018/002753, filed Jan. 29, 2018, which claims priority to Japanese patent application No. 2017-014668, filed Jan. 30, 2017, the entire disclosure of which is herein incorporated by reference as a part of this application.

FIELD OF THE INVENTION

The present invention relates to a bioabsorbable stent that is implanted in a stenosis part or an occlusion part, especially in the coronary arteries, in lumen of living body so as to keep the inserted part open, and to be gradually degraded in the living body.

BACKGROUND ART

The ischemic heart diseases (myocardial infarction, angina, etc.) caused by stenosis and occlusion of the coronary arteries are critical diseases which disturb supply of the blood (nutrition, oxygen, etc.) to a cardiac muscle, and are mentioned to the second place of the cause of Japanese death. As medical treatment of these disease, there have been widely used surgeries with low invasiveness using a catheter (percutaneous transluminal coronary angioplasty), not a surgical operation to open chest part (coronary-arteries bypass surgery). Especially, since a coronary-arteries stent placement has a small recurrence rate of stenosis (re-stenosis) compared with the conventional balloon formation, the stent replacement is regarded as the most promising remedy.

However, although coronary-arteries stent surgery gains popularity nowadays, there have been still many cases to cause complications at a certain period of postoperative time. The reason for this is considered that the stent made of cobalt chrome alloy body or stainless-steel body remains in the affected part with allowing intravascular wall open after being placed, so that the stent suppresses original blood vessel movement (pulsation), and continuously gives mechanical and chemical stimuli to the intravascular wall. In the medical front line, there has been expanding expectation for bioabsorbable stents as new medical equipment to solve the problem, i.e., the bioabsorbable stent having validity and safety to medical treatment for ischemic heart disease while enabling recovery of blood vessel movement after a certain period of postoperative time. A bioabsorbable stent is sometimes called as a bioabsorbable scaffold in recent years. Likewise, the bioabsorbable stent described here means a bioabsorbable scaffold.

Since the bioabsorbable stent has the innovative function to self-decompose gradually through the recovery process of the affected part, the bioabsorbable stent is a promising device being capable of cancelling the above-mentioned stimuli at an early stage, and making the affected part to regain normal blood vessel movement. This function is also advantageous to shorten a dosing period of antiplatelet agent for preventing complications, as well as to enhance the flexibility of the choice in postoperative re-medical treatment.

The bioabsorbable stents can be divided roughly into two types, made of polymer (nonmetallic) body or metal body. The polymer stents mainly made of polylactic acid first acquired the CE mark in Europe in 2010 in advance of metal stents. As a result, the polymer stents have been sold in 100 or more nations in the world including Japan as of 2016. However, the polymer stent described in Patent Document 1 has a problem that such a stent is weaker in strength than metal stents, resulting in insufficient bearing power, i.e., radial force of blood vessel. Even if the bioabsorbable polymer stent would achieve a radial force equivalent to that of the metal stent by enlarging thickness (strut), such a stent is not practical because of increased restenosis rate as well as deterioration in delivery of the stent to the affected part. The stent with a larger strut (for example, 150 μm) is reported to be inappropriate for application to the coronary arteries with a small caliber of 3 mm or less, to have low flexibility, and to be a cause of re-stenosis or stent thrombosis due to defect from excessive expansion of blood vessel wall.

On the other hand, the bare metal stent of a bioabsorbable magnesium alloy body also has a problem that mechanical strength is spoiled immediately during expansion in an aqueous solution because of acceleration of decomposition (corrosion) throughout the surface where water molecules are in contact. Accordingly, such a bioabsorbable magnesium stent has difficulty in practical application. The decomposition rate of a magnesium alloy in the living body environment is much faster than that of a polylactic acid. Considering the requirement to maintain sufficient blood vessel bearing power (radial force) for three to six months after stent implant, the bioabsorbable magnesium has by no means suitable characteristics. Patent Document 2 discloses that in the bioabsorbable medical implements which use magnesium or a magnesium alloy as a stent body, the decomposition rate of the stent body is adjustable by using an oxide film (oxide coat) formed on the surface of the stent body by ozone oxidation treatment.

Patent Document 3 describes, as a method of controlling corrosion of a magnesium alloy body containing aluminum and rare earth by a waterproofing barrier, a treatment in which a magnesium fluoride layer and a chemical conversion coating layer (aluminum oxide, cerium oxide, etc.) are formed on the body surface.

Patent Documents 4 and 5 disclose that a biodegradable polymer coating formed on the body surface can be used to adjust the decomposition rate of the body.

These attempts described in Patent Documents 4 and 5 should have suppressed the rise of pH caused by corrosion of magnesium alloy, but such attempts sometimes have ended up fatal damage in physical properties (particularly radial force) of the stent body.

RELATED ART DOCUMENT

Patent Documents

Patent Document 1 Japan patent No. 2842943
Patent Document 2 JP Laid-open Patent Publication No. 2013-215332
Patent Document 3 US2016/0129162A1
Patent Document 4 Japan patent No. 5425364
Patent Document 5 Japan patent No. 5701497

SUMMARY OF THE INVENTION

Problems to be Solved by the Invention

Since the magnesium alloy indicated by Patent Document 3 contains aluminum or rare earth, such a magnesium alloy may have a problem in respect of the safety to humans. Therefore, it is required to use the magnesium alloy which has the controlled biodegradability and is excellent in deformability, without containing aluminum and rare earth.

Since the magnesium fluoride ($MgF_2$) layer formed by fluoridation processing to the magnesium alloy surface in Patent Document 3 has very low solubility to water, the magnesium fluoride ($MgF_2$) layer is expected to exert outstanding corrosion resistance effect. However, the inventors of the present invention found that the corrosion rate of a magnesium alloy changed greatly depending on the surface quality of the core structure of a stent. For example, the inventors have been found that although Patent Document 3 indicates corrosion resistance of the magnesium fluoride layer formed by fluoridation processing, the surface quality achieved by the smooth surface treatment by electrolytic polishing causes a distinguishable corrosion resistance; and that uneven surface causes pitting corrosion (local corrosion), and brings about intense damage to a stent body by accelerative corrosion.

One of factors is an extremely small gap which arises in an interface between the stent body and the polymer layer during stent expansion. The gap problematically causes local pH rise accompanied by stay of corrosion products, such as magnesium hydroxide and hydrogen gas. Further, it is thought that the uneven surface caused by a crack would serve as a trigger of pitting corrosion (local corrosion). Unless the adhesiveness between the stent body and the polymer layer is improved, neither of the phenomena can be fundamentally solved.

Furthermore, the inventors have found that the magnesium fluoride layer formed on the surface of the stent body comprising a magnesium alloy enhances the adhesiveness of biodegradable polymer to the stent body so as to prevent causing gaps in the interface between the stent body and the polymer layer accompanied by stent expansion. For example, the polymer coated on the surface of the stent body in Patent Documents 4 and 5 would be a cause of accelerating corrosion due to poor adhesiveness of the polymer to the stent body.

The object of the present invention is to provide a bioabsorbable magnesium alloy stent (1) by obtaining a magnesium alloy without rare earth and aluminum, that is safe to humans and highly excellent in deformability, (2) by forming a core structure (stent scaffold or backbone) with a smooth surface from the alloy, and (3) by forming a uniform corrosion-resistant layer on the above-mentioned core structure, wherein the stent even in an expanded state can sustain physical properties in a simulated plasma solution (EMEM+ 10% FBS) at 37° C. under 5% $CO_2$ atmosphere as well as in coronary arteries of pig over one month, and wherein (4) the stent has an improved adhesiveness between the above-mentioned corrosion-resistant layer and a biodegradable polymer.

Means for Solving the Problem

In order to achieve the above-mentioned object, as a result of intensive study for composition of a magnesium alloy which forms a stent body and a surface treatment of the magnesium alloy, the inventors of the present invention have reached the present invention.

A first aspect of the present invention is a bioabsorbable stent having a core structure comprising a magnesium alloy and a corrosion resistant layer on the core structure, wherein the core structure is formed from the magnesium alloy containing 90 mass % or more of Mg as a main component, Zn, Zr, and Mn as accessory components, and 30 ppm or less of unavoidable impurities selected from the group consisting of Fe, Ni, Co, and Cu, and the alloy excluding (free from) aluminum and at least one sort of rare earths selected from the group consisting of Sc, Y, Dy, Sm, Ce, Gd, and La; the core structure has a smooth surface; and the corrosion resistant layer has a hydrophilic smooth surface containing magnesium fluoride ($MgF_2$) as a main component. According to the present invention, the core structure means a tubular member (stent scaffold member) which is formed spirally and has an expansive property. According to the present invention, the thickness of the corrosion resistant layer is preferably 1 μm or larger and 10 μm or smaller.

According to a second aspect of the present invention, in the first aspect, the accessory components preferably contain 1.0 to 2.0 mass % of Zn, 0.05 to 0.80 mass % of Zr, 0.05 to 0.40 mass % of Mn.

According to a third aspect of the present invention, in the second aspect, the magnesium alloy preferably further contains 0.005 to 0.20 mass % of Ca.

According to a fourth aspect of the present invention, in any one of the first to third aspects, the magnesium alloy preferably contains unavoidable impurities selected from the group consisting of Fe, Ni, Co, and Cu, each of which is contained at a proportion of less than 10 ppm.

According to a fifth aspect of the present invention, in any one of the first to fourth aspects, the smooth surface preferably has a surface roughness of 0.20 μm or smaller.

According to a sixth aspect of the present invention, in any one of the first to fifth aspects, a biodegradable polymer layer is formed on at least a part of the hydrophilic smooth surface of the corrosion resistant layer.

According to a seventh aspect of the present invention, in the sixth aspect, it is preferred that the stent is free from a gap between the corrosion resistant layer and the biodegradable polymer layer.

According to an eighth aspect of the present invention, in the sixth or seventh aspect, the biodegradable polymer layer preferably contains an intimal thickening inhibitor.

According to a ninth aspect of the present invention, in the eighth aspect, the intimal thickening inhibitor is preferably at least one member selected from the group consisting of sirolimus, everolimus, biolimus A9, zotarolimus, and paclitaxel.

According to a tenth composition of the present invention, in a method of producing a bioabsorbable stent having a core structure comprising a magnesium alloy, the method comprises: forming a core structure comprising a magnesium alloy containing 90 mass % or more of Mg as a main component, Zn, Zr, and Mn as accessory components, and 30 ppm or less of unavoidable impurities (Fe, Ni, Co, and/or Cu), and excluding aluminum and rare earth (Sc, Y, Dy, Sm, Ce, Gd, and La); carrying out electrolytic polishing of the obtained core structure; and forming a corrosion resistant layer having a hydrophilic smooth surface which contains magnesium fluoride ($MgF_2$) as a main component by fluoridation processing of the core structure surface.

According to an eleventh aspect of the present invention, in the tenth aspect, the electrolytic polishing is preferably carried out until the surface of the core structure comes to have a surface roughness (Ra) of 0.20 μm or less. It is preferred to carry out the electrolytic polishing, until the surface of the core structure comes to have a surface roughness (Ra) of 0.10 μm or less.

Any combination of at least two constituent elements disclosed in the claims and/or the specification is included in the present invention. In particular, any combination of two or more of the appended claims should be equally construed as included within the scope of the present invention.

Effect of the Invention

The stent of the first aspect of the present invention is excellent in deformability because the stent contains a predetermined amount of Zn, Zr, and Mn in combination with 90 mass % or more of Mg. Further, the stent of the first aspect of the present invention excels in safety to humans because unavoidable impurities selected from the group consisting of Fe, Ni, Co, and Cu is contained in 30 ppm or less, and the stent is free from rare metals and aluminum. Magnesium content is more preferably 93 mass % or more, and still more preferably 95 mass % or more.

According to the first aspect of the present invention, since the above-mentioned core structure has a high level smooth surface Ra of 0.20 μm or smaller (preferably Ra of 0.10 μm or smaller) as a pretreatment for forming the above-mentioned corrosion resistant layer so as to attain a smooth corrosion resistant surface of the stent, the obtained stent has a good capability of following physical change during diameter reduction and diameter expansion.

The stent has a magnesium fluoride layer throughout a smooth surface of the core structure formed of the magnesium alloy with the above-mentioned composition. The stent not only excels in anti-corrosiveness, but also excels in deformation followability. In addition, the hydrophilicity of the magnesium fluoride layer enhances adhesiveness between the biodegradable polymer layer formed on the magnesium fluoride layer and the magnesium fluoride layer.

The corrosion resistant layer preferably has a thickness of 1 μm or larger and 10 μm or smaller. The above-mentioned corrosion resistant layer enables to obtain a stent having desired anti-corrosiveness, deformation followability, and adhesiveness with polymer coating.

In the stent according to the first aspect of the present invention the above-mentioned core structure and the corrosion resistant layer are made of biodegradable materials, so that the stent is gradually biodegradable in the living body over about one year.

According to the first aspect of the present invention, it is possible to obtain a stent being capable of having a significant difference in temporal reduction of the radial force in the plasma imitation solution (EMEM+10% FBS) at 37° C. under 5% $CO_2$ atmosphere, as well as in coronary arteries of pigs as compared with a stent (bare core structure) which is outside the scope of the present invention, so that the stent according to the first aspect of the present invention can maintain radial force at least one month and longer (e.g., for three to six months).

According to the second aspect of the present invention, a predetermined amount of Zn, Zr, and Mn contained as accessory components enables to form a fine alloy structure, so as to make it possible to obtain a magnesium alloy stent excellent in both physical properties and corrosion resistance.

According to the third aspect of the present invention, a predetermined amount of Ca contained as an accessory component enables to obtain a stent with improved corrosion resistance while keeping the physical properties of the magnesium alloy.

According to the fourth aspect of the present invention, a small amount of each of the unavoidable impurities (Fe, Ni, Co, Cu) of 10 ppm or less is effective to suppress corrosion of the magnesium alloy.

According to the fifth aspect of the present invention, the core structure has a highly smooth surface with a surface roughness (Ra) of 0.2 μm or less (preferably 0.10 μm or less, still more preferably 0.05 μm or less) so as to make it possible to form a uniform layer of a magnesium fluoride layer on the magnesium alloy layer, resulting in excellent corrosion resistance.

According to the sixth aspect of the present invention, the biodegradable polymer may be a polyester.

According to the seventh aspect of the present invention, since the stent is free from gaps between the corrosion resistant layer and the biodegradable polymer layer, the stent can effectively suppress corrosion.

According to the eighth and ninth aspects of the present invention, by forming the above-mentioned coating layer containing the biodegradable polymer and the intimal thickening inhibitor throughout or in part of the surface of the above-mentioned corrosion resistant layer, it is possible to obtain a stent which attains intimal thickening inhibition without accelerating the corrosion of the core structure.

According to the tenth and eleventh aspects of the present invention, since a magnesium fluoride layer is formed on the surface of the core structure having a smooth surface formed by electrolytic polishing, the core structure realizes high anti-corrosiveness.

Any combination of at least two constituent elements disclosed in the claims and/or the specification is included in the present invention. In particular, any combination of two or more of the appended claims should be equally construed as included within the scope of the present invention.

BRIEF DESCRIPTION OF THE DRAWINGS

This invention will be more clearly understood from the following description of preferred embodiments with reference to the attached drawings. However, the embodiments and the drawings are given only for the purpose of illustration and explanation, and should not be used to limit the scope of the invention. The scope of the invention is determined by the appended claims. In an accompanying drawing, the same reference number in a plurality of drawings shows the same portion.

DESCRIPTION OF EMBODIMENTS

Basic Structure of Stent

Figure 4:
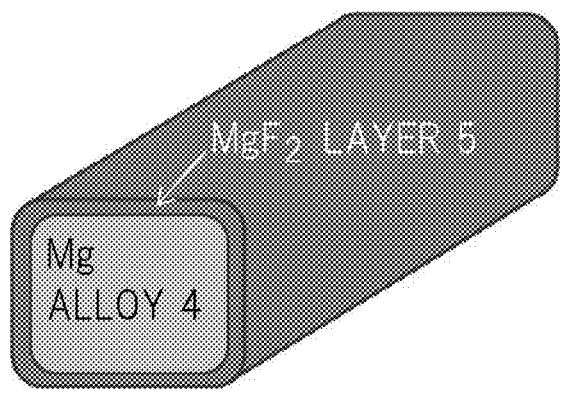
FIG. 4 is a schematic view showing elements of the stent according to the present invention.
Figure 5:
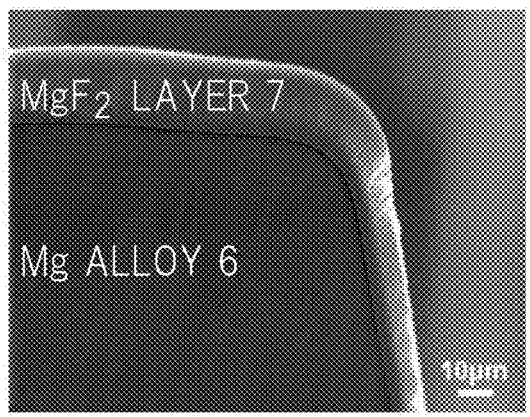
FIG. 5 is an SEM observation sectional image of the stent according to the present invention.

A stent of the present invention, as shown in FIG. 4, comprises: a core structure 4 comprising a magnesium alloy (Mg alloy), and a corrosion resistant layer 5 mainly comprising a magnesium fluoride ($MgF_2$) layer formed throughout the surface of the above-mentioned core structure. FIG. 5 shows a cross-sectional image of the core structure (comprising a Mg alloy layer 6 and a $MgF_2$ layer 7) according to the present invention and reveals integration of the $MgF_2$ layer to the Mg alloy layer 6.

The technical elements of the above-mentioned aspect comprise an element to select a composition of magnesium alloy for a core structure excellent in deformability while having biodegradability, an element to form the above-mentioned corrosion resistant layer containing $MgF_2$ as the main component throughout the surface of the core structure in order to control corrosion of the core structure of the selected magnesium alloy, an element to determine a surface configuration of the core structure and the corrosion resistant layer in order to prevent deterioration in mechanical strength due to accelerative corrosion, and an element to secure adhesiveness of the bioabsorbable materials to the surface of the core structure.

Magnesium Alloy

The core structure of the stent of the present invention is formed from a bioabsorbable magnesium alloy. As a bioabsorbable metal, although pure magnesium, a magnesium alloy, a malleable iron, an iron alloy, and others may be mentioned, the magnesium alloy is preferable considering bioabsorbability and mechanical properties.

In the present invention, the core structure of a stent is formed from a magnesium alloy containing 90 mass % or more of magnesium (Mg) as a main component, zinc (Zn), a zirconium (Zr), and manganese (Mn) as accessory components, and 30 ppm or less of unavoidable impurities selected from the group consisting of iron (Fe), nickel (Ni), cobalt (Co), and copper (Cu), and excluding aluminum and at least one sort of rare earths selected from the group consisting of scandium (Sc), yttrium (Y), dysprosium (Dy), samarium (Sm), cerium (Ce), gadolinium (Gd), and lanthanum (La). This specific composition secures safety to living body as well as mechanical properties. From the viewpoint of enhancing living body safety and mechanical property, the content of Mg is preferably 93 mass % or more, and still more preferably 95 mass % or more. The harmfulness to humans can be prevented by excluding at least one sort of rare earths of Sc, Y, Dy, Sm, Ce, Gd, and La, and aluminum.

Accessory Components

It is preferred that accessory components include 1.0 to 2.0 mass % of Zn, 0.05 to 0.80 mass % of Zr, and 0.05 to 0.40 mass % of Mn.

Zn is added to form a solid-solution with Mg and to enhance strength and elongation of the alloy. Where the amount of Zn is too small, intended effect cannot be obtained. The too large amount of Zn may be unpreferable, Zn content may exceed the solid-solubility limit, resulting in non-desired formation of Zn-rich precipitates that reduce the corrosion resistance.

Zr scarcely forms solid-solution with Mg, and forms fine-grained precipitates, thereby preventing coarsening of crystal grains of alloy. Where the amount of Zr is too small, effects of Zr addition cannot be obtained. The too large amount of Zr may be unpreferable because precipitates are formed in excessive amount, thereby reducing processability of the alloy.

Mn has effects of refining grain size of alloy and enhancing corrosion resistance of alloy. Where the amount of Mn is too small, intended effect cannot be obtained. The too large amount of Mn may be unpreferable because workability in plastic working is degraded.

Calcium (Ca) may be further added to the above-mentioned accessory components at a proportion of 0.05 mass % or more and less than 0.20 mass %. Ca may be optionally added into the magnesium alloy, since the addition of Ca allows to expect enhancement of corrosion resistance while maintaining strength of the magnesium alloy. Where the amount of Ca is too small, the addition of Ca provides no effects. The too large amount of Ca may be unpreferable because precipitates tend to be formed, making it impossible to obtain complete solid-solution of single phase.

Unavoidable Impurities

It is preferred to control the amount of unavoidable impurities. Since Fe, Ni, Co, and Cu enhance corrosion of the magnesium alloy, it is preferable to control an amount of each of these elements to be less than 10 ppm, more preferably 5 ppm or less. Preferably, the total amount of unavoidable impurities is controlled to be 30 ppm or less, more preferably 10 ppm or less. The amount of unavoidable impurities may be determined, for example, by ICP emission spectrometry.

Production of Magnesium Alloy

Figure 1A:
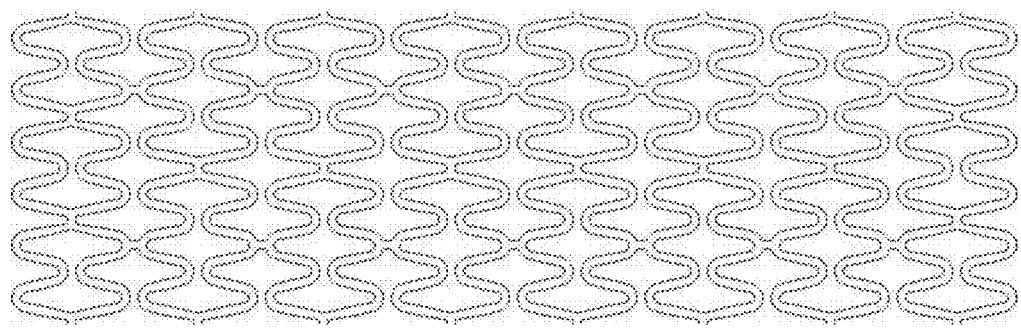
FIG. 1A is a plan view showing an example of the scaffold structure of the stent according to the present invention.
Figure 1B:
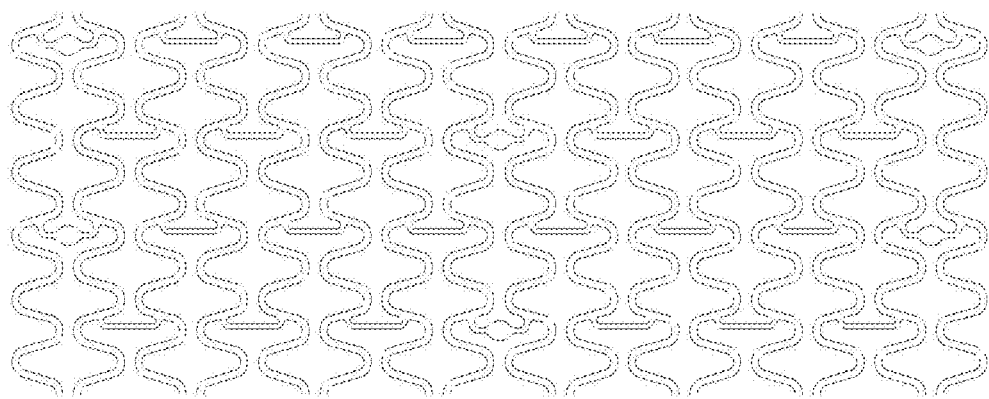
FIG. 1B is a plan view showing another example of the scaffold structure of the stent according to the present invention.
Figure 2:
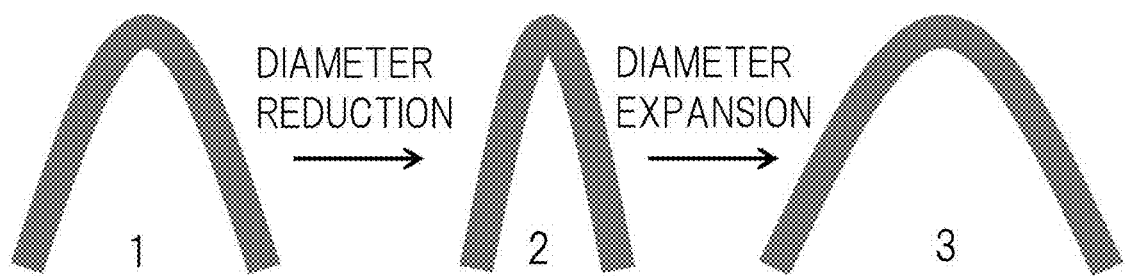
FIG. 2 is a schematic view showing a physical change of the stent according to the present invention during diameter reduction and expansion.

The magnesium alloy can be produced, in accordance with usual production method of magnesium alloys, throwing ground metals or alloys of Mg, Zn, Zr, and Mn, and where necessary Ca, into a crucible, melting the ground metals and/or alloys in the crucible at a temperature of 650 to 800° C. to form a molten alloy, and casting the molten alloy. Where necessary, the cast alloy is subjected to solution heat treatment. Rare earth element-free and aluminum-free metals are used as the ground metals. It is possible to suppress the amounts of Fe, Ni, and Cu in the impurities by the use of ground metals with high purity. Fe, Ni, and Co in the impurities of molten alloy may be removed by iron-extraction treatment. In addition, it is possible to use ground metals produced by distillation refining Scaffold Shape of Stent Thus-obtained ingot can acquire a scaffold shape (core structure) of a stent by extrusion processing of the ingot under melt to obtain a tubular magnesium alloy, followed by laser-processing of the tubular magnesium alloy. The stent of the present invention may have various scaffold shapes including conventional shapes. The scaffold shapes shown in FIGS. 1A and 1B are exemplified.

Electrolytic Polishing: Smooth Surface Formation

As a pretreatment for forming a corrosion resistant layer having a smooth surface, the laser-processed stent scaffold is preferably polished by using the scaffold as a positive electrode with placing metal plates as negative electrode in an electrolysis solution, and electrically connecting them with applying a voltage so as to produce a core structure with an arbitrary size.

Corrosion Resistant Layer Formation

In order to form a corrosion resistant layer having a smooth surface, the core structure surface having a specular surface by electrolytic polishing is subjected to fluoridation processing. As far as a $MgF_2$ layer can be formed, the conditions for fluoridation processing are not specifically limited. For example, a core structure can be immersed into a treating solution, such as a hydrofluoric-acid aqueous solution. It is preferred to immerse the core structure with shake, for example, at 50 to 200 ppm, preferably 80 to 150 ppm. Then, the core structure on which $MgF_2$ layer is formed is taken out from the solution, followed by washing sufficiently with cleaning fluid (for example, acetone aqueous solution), for example, by ultrasonic cleaning Where the washed core structure is subjected to drying, it is preferred that the core structure is dried at 50 to 60° C. for 24 hours or longer under vacuum.

Surface Feature of Corrosion Resistant Layer

The corrosion resistant layer of the stent according to the present invention preferably has a surface roughness (Ra) of 0.20 μm or less in view of corrosion resistance and deformation followability. Where the stent has a smaller Ra, i.e., has a surface with high-level smooth quality, the stent has an improved deformation followability. Accordingly, the surface roughness (Ra) is more preferably 0.10 μm or less and still more preferably 0.05 μm or less.

Here, Ra means the arithmetic average roughness measured in accordance with JIS B 0601:2001. The smooth surface here is defined as a smooth surface having an Ra of 0.20 μm or less (also called as specular surface).

Composition of Corrosion Resistant Layer

The corrosion resistant layer of the stent according to the present invention comprises 90% or more of $MgF_2$ as the main component. Further, a corrosion resistant layer contains oxide and hydroxide such as MgO and $Mg(OH)_2$, can improve adhesiveness between the corrosion resistant layer ($MgF_2$ layer) and a biodegradable polymer layer formed on the corrosion resistant layer so as to enhance deformation followability. The corrosion resistant layer may contain an oxide and a hydroxide of a metal contained in the above-mentioned stent and other than magnesium. It should be noted that the highly smooth level of the corrosion resistant layer surface enables to suppress corrosion of the core structure even if the core structure is subjected to physical deformation, such as diameter reduction and diameter expansion. That is, what is important is that the corrosion resistant layer formed on the surface of the core structure has deformation followability to the core structure as well as adhesiveness to a polymer coating. Even if corrosion resistance would be demonstrated in a core structure without deformation, such a demonstrated corrosion resistance is not sufficient for the required stent performance.

Layer thickness of Corrosion Resistant Layer

The layer thickness of the corrosion resistant layer of the stent according to the present invention is preferably 1 μm or larger in view of corrosion resistance, and 10 μm or smaller in view of deformation followability. The layer thickness of the corrosion resistant layer of the stent according to the present invention is more preferably 5 μm or smaller and still more preferably 3 μm or smaller in order to avoid too high corrosion resistance that may spoil bioabsorbability.

Coating Layer

The stent according to the present invention may comprise a coating layer containing a biodegradable polymer and an intimal thickening inhibitor on a part or a whole surface of the corrosion resistant layer. As the biodegradable polymer, there may be mentioned polyesters etc., and examples of the biodegradable polymer may include a poly(L-lactic acid) (PLLA), a poly(D, L-lactic acid) (PDLLA), a polylactic acid-glycolic acid (PLGA), a polyglycolic acid (PGA), a polycaprolactone (PCL), a poly (lactic acid-ε-caprolactone) (PLCL), a polyglycolic acid-ε-caprolactone (PGCL), a poly(p-dioxanon), a poly(glycolic acid-trimethylenecarbonate), a poly(β-hydroxybutyric acid), and the like.

Intimal Thickening Inhibitor

As the intimal thickening inhibitor there may be mentioned sirolimus, everolimus, biolimus A9, zotarolimus, paclitaxel, and the like.

Stent Performance

The stent comprising the corrosion resistant layer having a smooth surface as described above can significantly deter temporal deterioration in radial force of the core structure in a simulated plasma solution (EMEM+10% FBS) at 37° C. under 5% $CO_2$ atmosphere as well as temporal deterioration in radial force of the core structure implanted in coronary arteries of pig in comparison with the stents which are outside the scope of the present invention or the stents without corrosion resistant layer (bare core structure) as shown in the below-mentioned Examples and Comparative Examples.

EXAMPLE

Hereinafter, the present invention will be described by referring to Examples in detail. It should be noted that the present invention be not limited to the following Examples.

Each of the Examples and Comparative Examples had a stent scaffold design shown in FIG. 1A. It should be noted that the same tendency was obtained as for the scaffold design shown in FIG. 1B.

(1) Preparation of Magnesium Alloy that Constitutes Stent

Calcium and high purity ground metals of Mg, Zn, Mn, and Zr were prepared as raw materials. Respective components were weighted so as to constitute the below-described component concentration, and were thrown into a crucible, and were molten and stirred at 730° C. Thus obtained melt was cast to form an ingot. Rare earth elements and aluminum were not contained in the raw materials even as unavoidable impurities.

The Mg (magnesium) was provided from a magnesium ground metal with purity level of 99.99% with low concentration of impurity Cu. Iron-extraction treatment was carried out in the crucible to remove iron and Ni from the melt.

Impurity concentrations of the thus obtained samples were measured using an ICP emission spectrometer (AGILENT 720 ICP-OES made by Agilent Technologies).

The component concentration (mass %) of the obtained ingot is as follows.

Mg: Balance; Zn: 1.5%; Mn: 0.4%; Zr: 0.4%, and Fe, Ni, Co, and Cu were contained in the above-mentioned ingot at the following concentration as unavoidable impurities, i.e., Fe: 5 ppm, Ni: 5 ppm, Co: ND (below a detection limit), and Cu: 1 ppm.

(2) Stent Scaffold Production

The above-mentioned magnesium alloy ingot was subjected to extrusion processing to obtain a small tube with a thickness of 150 μm (outer diameter of 1.8 mm/inner diameter of 1.5 mm), followed by laser processing so as to form a small tube with a shape shown in FIG. 1A as a stent scaffold.

(3) Electrolytic Polishing

Thus-obtained stent scaffold was surface-cleaned with an acidic solution to remove the oxide adhered to the scaffold. Then, the obtained stent scaffold was immersed in an electrolysis solution as a positive electrode with placing metal plate as a negative electrode, and the direct-current power was applied between the stent scaffold and the metal plates for attaining specular surface by mirror-polishing so as to obtain a stent scaffold with a thickness of 100 μm (outer diameter of 1.75 mm/inner diameter of 1.55 mm) with a smooth surface. In order to stabilize mucus solution layer under voltage impression, the electrolysis solution was agitated and controlled to have a stable (fixed) temperature. In order to control air bubbles generated at the negative electrode, impression and cutting of voltage were repeated at a certain frequency. It should be noted that where air bubbles detached from the negative electrode attach to the stent scaffold, they cause poor surface accuracy.

(4) Test Samples

Stent samples of Examples and Comparative Examples were produced from the above-described stent scaffolds. Each of the stent sample was set up (crimped) at a balloon attached to the distal end of a balloon catheter so as to have an outer diameter of 1.2 mm Evaluation of Corrosion Resistance and Deformation Followability The core structure with a surface having enhanced corrosion resistance and deformation followability can delay the decline of the mechanical strength of the core structure due to the accelerative corrosion of the core structure in blood vessels. Therefore, it is possible to evaluate corrosion resistance and deformation followability by measuring weight change, radial force residual ratio, and recoil value of the core structure in the simulated plasma solution (EMEM+ 10% FBS) at 37° C. under 5% $CO_2$ atmosphere, as well as in coronary arteries of pigs.

Evaluation of Adhesiveness of Corrosion Resistant Layer to Polymer Coating

The corrosion resistant layer with good adhesiveness to a polymer coating has a surface having a relatively high surface free energy and hydrophilicity. Therefore, adhesiveness of corrosion resistant layer to polymer coating can be evaluated by measuring water contact angle on the surface. In addition, appearance change in polymer coating layer after diameter reduction and diameter expansion can be observed.

Evaluation in Weight Change and Radial Force Residual Ratio

Figure 3:
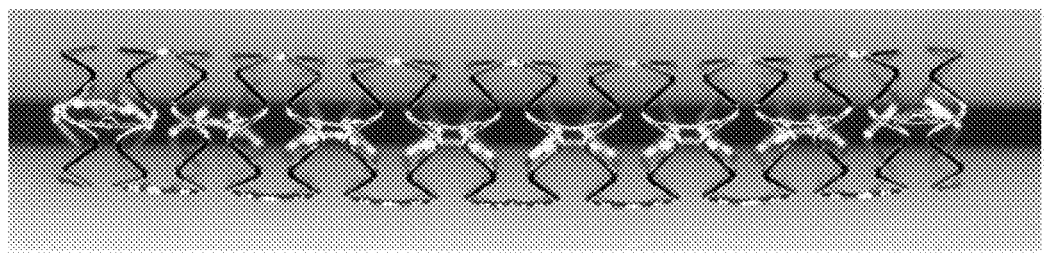
FIG. 3 is an example of microscope observation image of the stent according to the present invention that was expanded to 3 mm in inner diameter.

A stent sample crimped at a balloon catheter was immersed in a 37° C. simulated plasma solution (EMEM+ 10% FBS) for 2 minutes, and then was uniformly expanded to have an inner diameter of 3 mm (FIG. 3), and was shaken at 100 rpm with keeping immersion at 37° C. under 5% $CO_2$ atmosphere. It means that the stent at this stage was exposed to plastic elastic deformation (physical change) by crimping (reducing diameter) to a balloon catheter and stenting (expanding diameter). The sample was taken out at 28 days after immersion, and the radial force of the sample was measured with SEM observation of the surface. Further, the sample was cleaned ultrasonically with chromic acid solution to remove corrosion products such as magnesium hydroxide, etc., and the weight change of the core structure was evaluated (n=5). As to the radial force measurement, RX550/650 (produced by Machine Solutions Inc.) was used.

Implant Test in Pig Coronary Arteries

Each of the stent samples (Example 1 and Comparative Example 2) crimped at the balloon catheter was implanted in six coronary arteries (LAD, LCX) of a white pig (50-55 kg), and was expanded at the part having an intravascular diameter of about 3 mm. Two coronary arteries were selected out of the three coronary arteries per animal, and two stent samples per animal were detained as shown in Table 1.

TABLE 1

| Combination of Implanted Sites and Samples | | | |
| --- | --- | --- | --- |
| | LAD | LCX | RCA |
| White Pig 1 | Example 1 | Comparative Example 2 | |
| White Pig 2 | | Example 1 | Comparative Example 2 |
| White Pig 3 | Comparative Example 2 | | Example 1 |

Recoil Value Evaluation of Stent Implanted in Pig Coronary Arteries

Immediately after implant, the status in which the stent was in contact to the vessel wall was confirmed and then the inner diameter area (a) of the implanted stent was measured using an angiography apparatus. At 28 days after implant of the stent in pig coronary arteries, an inner diameter area (b) of the detained stent was measured using an angiography apparatus, then the recoil value (n=3) of the stent was calculated by the following formula.

$$\text{Recoil value} = (a-b)/a$$

Example 1

Figure 6A:
FIGS. 6A, 6B and 6C are schematic views showing a surface quality of the stent according to the present invention and those of Comparative Examples 1 and 2, respectively.

A stent scaffold having an Ra of 0.57±0.18 μm was polished by electrolytic polishing so that the edge had a smooth (round) surface with an Ra of 0.05±0.01 μm, and then immersed in a 27 M hydrofluoric-acid aqueous solution (2 mL) and reciprocally moved at a rate of 100 rpm. Then, the stent was taken out after 24 hours, and subjected to ultrasonic cleaning sufficiently with acetone aqueous solution followed by drying the core structure for 24 hours at 60° C. under vacuum. The surface of the stent had a $MgF_2$ layer with a thickness of not more than 10 μm as shown in FIGS. 4, 5 and 6A. The significant difference in Ra was not observed between before fluoridation processing and after fluoridation processing. After crimping thus-obtained stent sample in the balloon catheter, ethylene oxide gas (EOG) sterilization was performed to the prepared sample. A total of five samples were prepared on the same conditions as this condition.

Example 2

A stent scaffold having an Ra of 0.57±0.18 μm was polished by electrolytic polishing to have an Ra of 0.20±0.01 μm, and then immersed in a 27 M hydrofluoric-acid aqueous solution (2 mL) and reciprocally moved at a rate of 100 rpm. Then, the stent was taken out after 24 hours, subjected to ultrasonic cleaning sufficiently with acetone aqueous solution followed by drying the core structure for 24 hours at 60° C. under vacuum. The surface of the core structure had a $MgF_2$ layer with a thickness of not more than 10 μm as shown in FIG. 6A. The significant difference in Ra was not observed between before fluoridation processing and after fluoridation processing. At the end, after crimping thus-obtained stent sample in the balloon catheter, EOG sterilization was performed to the prepared sample. A total of five samples were prepared on the same conditions as this condition.

Comparative Example 1

Figure 6B:
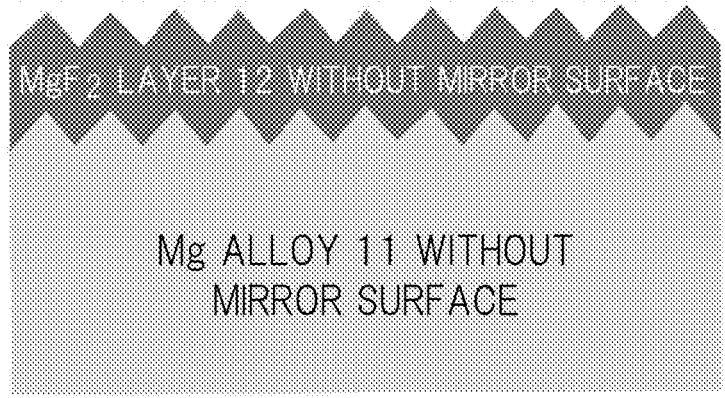

A stent scaffold having an Ra of 0.57±0.18 μm was polished by electrolytic polishing to have an Ra of 0.30±0.01 μm (un-smooth surface), and then immersed in a 27 M hydrofluoric-acid aqueous solution (2 mL) and reciprocally moved at a rate of 100 rpm. Then, the stent was taken out after 24 hours, subjected to ultrasonic cleaning sufficiently with acetone aqueous solution followed by drying the core structure for 24 hours at 60° C. under vacuum. The surface of the core structure had a $MgF_2$ layer with a thickness of not more than 10 μm as shown in FIG. 6B. The significant difference in Ra was not observed between before fluoridation processing and after fluoridation processing. At the end, after crimping thus-obtained stent sample in the balloon catheter, EOG sterilization was performed to the prepared sample. A total of five samples were prepared on the same conditions as this condition.

Comparative Example 2

Figure 6C:
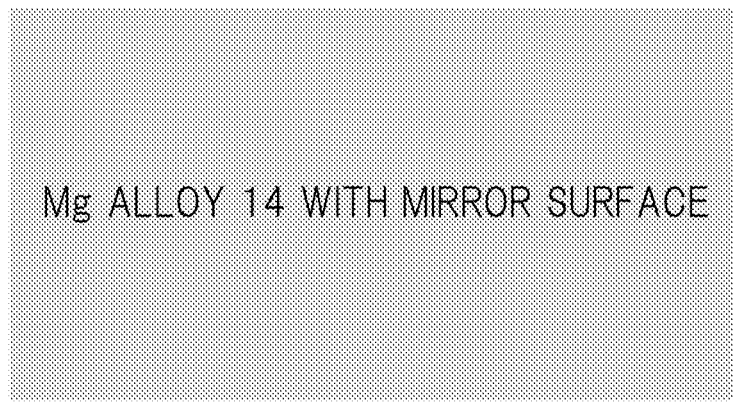

A stent scaffold having an Ra of 0.57±0.18 μm was polished by electrolytic polishing to have an Ra of 0.05±0.01 μm (FIG. 6C) was crimped at the balloon catheter, and then EOG sterilization was performed to the prepared sample. Five samples were prepared on the same conditions as this condition.

The stents used in Examples have the structure shown in FIG. 6A. The stents used in Comparative Example have the structures shown in FIGS. 6B and 6C, respectively. The stent shown in FIG. 6A comprises a core structure 8 of a bioabsorbable magnesium alloy, and a corrosion resistant layer 9 of $MgF_2$ with a smooth surface 10. The stent shown in FIG. 6B comprises a core structure 11 of a bioabsorbable magnesium alloy, and a corrosion resistant layer 12 of $MgF_2$ with un-smooth surface 13. The stent shown in FIG. 6C consists only of a core structure 14 of a bioabsorbable magnesium alloy, and had a smooth surface 15.

The composition and the evaluation results of corrosion resistance and deformation followability of the samples in Examples 1 and 2 and Comparative Examples 1 and 2 are shown in Table 2.

Table 2 Composition and Performance (Corrosion Resistance and Deformation Followability) of Samples In Examples 1-2 and Comparative Examples 1-2

Figure 7:
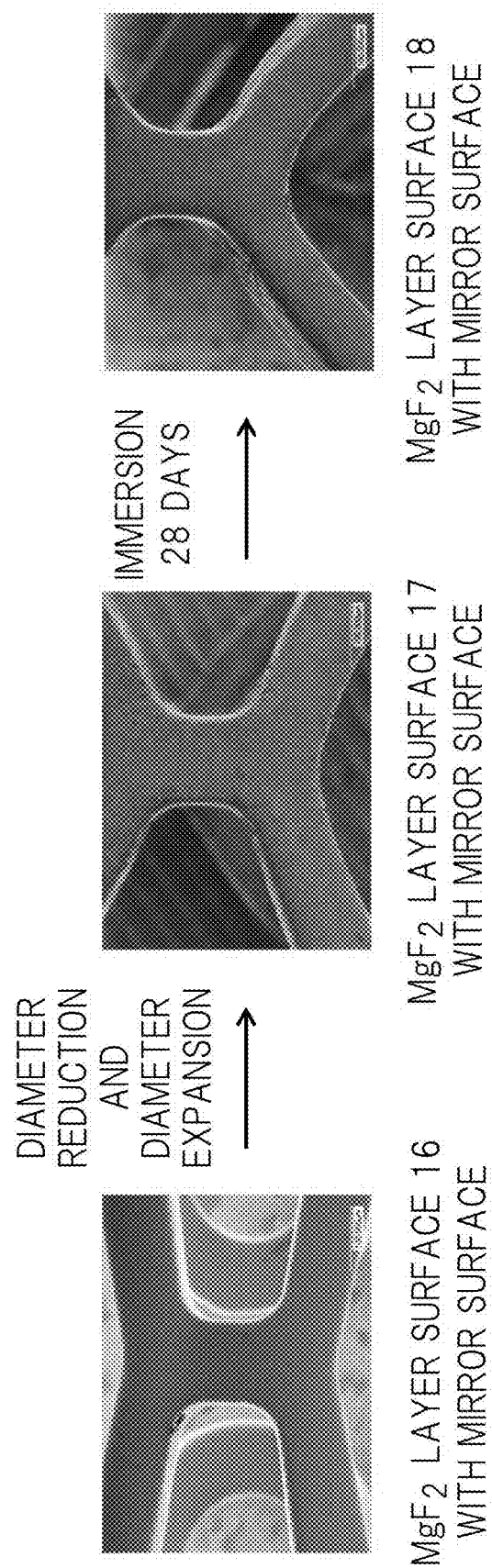
FIG. 7 is an SEM observation image of the stent (Example 1) according to the present invention used for in vitro test.
Figure 8:
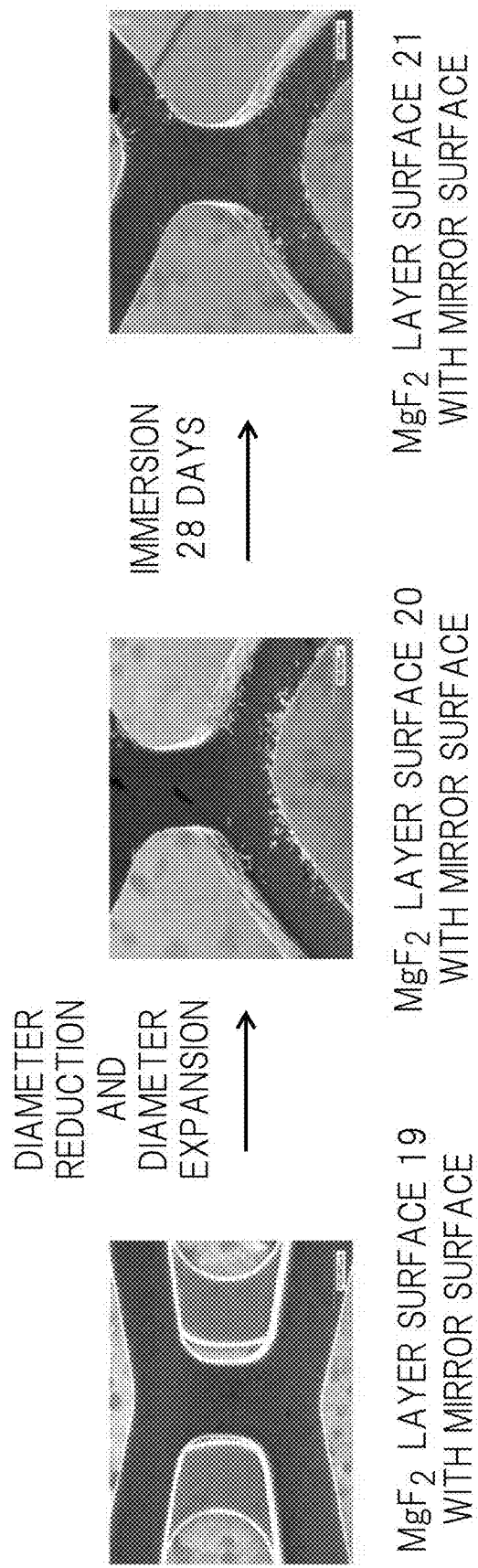
FIG. 8 is a SEM observation image of the stent (Example 2) according to the present invention used for in vitro test.

|  | Corrosion resistant layer | Performance | | Remarks |
|---|---|---|---|---|
|  |  | Corrosion resistance | Deformation followability |  |
| Ex. 1 (FIG. 6A) | $MgF_2$ Ra: 0.05 μm | Yes | Yes | FIG. 7 |
| Ex. 2 (FIG. 6A) | $MgF_2$ Ra: 0.20 μm | Yes | Yes | FIG. 8 |
| Com. Ex. 1 (FIG. 6B) | $MgF_2$ Ra: 0.30 μm | Yes | No | FIG. 9 |
| Com. Ex. 2 (FIG. 6C) | None Ra: 0.05 μm | No | — | FIG. 10 |

Stent Surface Observation Immediately After Expansion

Figure 9:
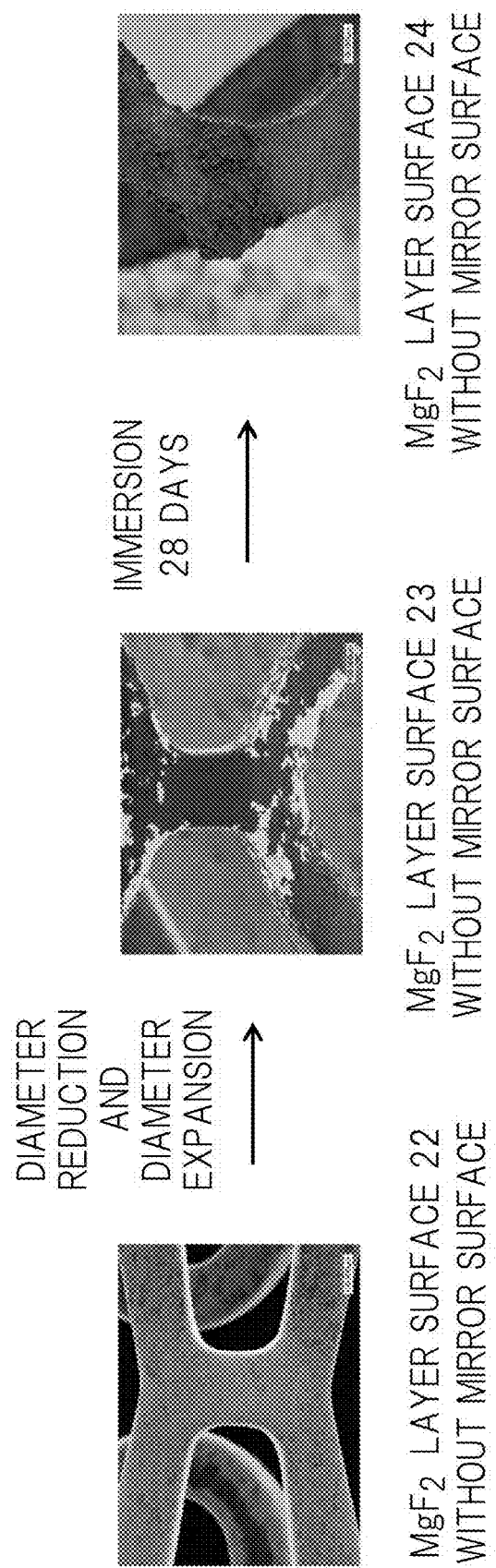
FIG. 9 is a SEM observation image of the stent (Comparative stent 1) used in vitro test.
Figure 10:
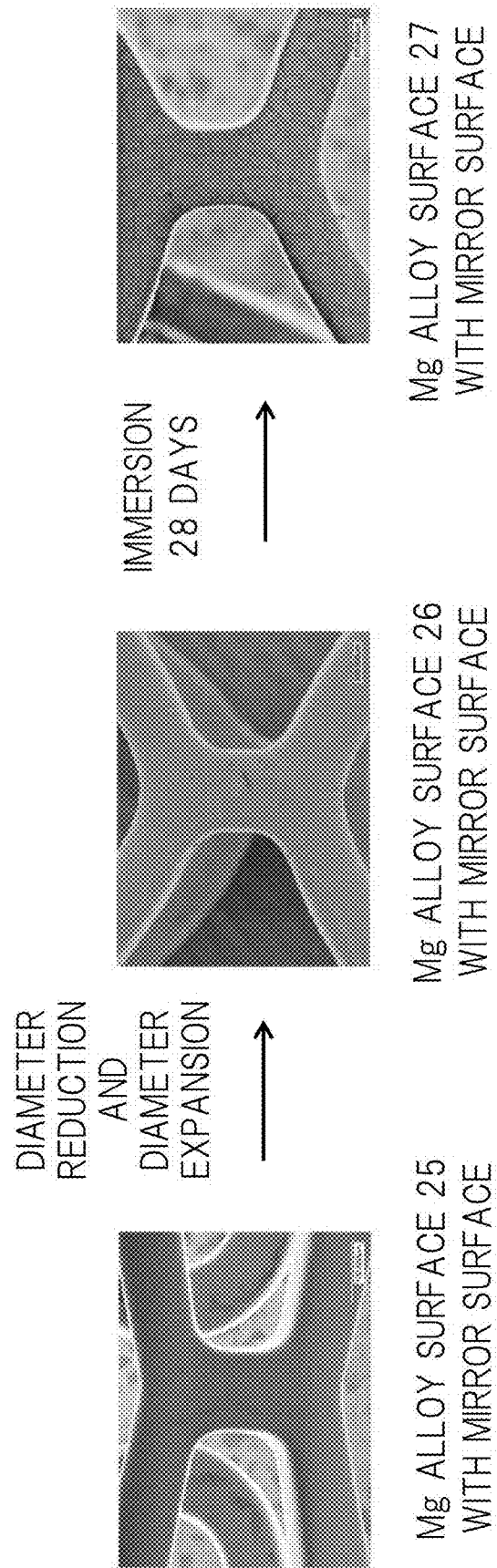
FIG. 10 is a SEM observation image of the stent (Comparative stent 2) used in vitro test.

The samples having the elements based on the present invention (Examples 1 and 2) did not cause serious damage (crack and fracture) in the corrosion resistant layers by sequential physical change of diameter reduction and diameter expansion (see FIGS. 7 and 8). Further, since hydrogen generation having a relationship with corrosion was not recognized in Examples 1 and 2, the results implied that corrosion resistance effect was attained. In addition, neither serious damage nor supersensitive corrosion was observed in the comparative sample (Comparative Example 2) without corrosion resistant layer (FIG. 10). These phenomena presumably originate from the smooth surface of the magnesium alloy and the uniform oxide layer formed on the smooth surface of the magnesium alloy. On the other hand, the corrosion resistant layer of the comparative sample (Comparative Example 1) outside from the present definition of the smooth surface caused crack after expansion (FIG. 9).

Stent Weight Change Before And After Immersion

The weights of each of the samples before immersion as well as at 28 days after immersion in the simulated plasma solution were measured. Table 3 shows the result of the weight residual ratio of the sample before and after immersion calculated based on the weight of the core structure before immersion. The weight of the sample before immersion was 5.92±0.32 mg.

TABLE 3

Weight Change of Stent Sample Before and After Immersion (Weight Residual Ratio [%])

|  | Before immersion | After immersion | Remarks |
|---|---|---|---|
| Ex. 1 | 100 | 95.6 ± 1.4 | FIG. 7 |
| Ex. 2 | 100 | 94.3 ± 2.9 | FIG. 8 |
| Com. Ex. 1 | 100 | 85.7 ± 3.0 | FIG. 9 |
| Com. Ex. 2 | 100 | 72.2 ± 6.2 | FIG. 10 |

Relative Evaluation of Stent at 28 Days After Immersion

The samples (Examples 1 and 2) with elements based on the present invention had significantly high weight residual ratios compared with those in the comparative samples (Comparative Examples 1 and 2) so that it was presumed that the corrosion resistant layer suppressed corrosion.

As shown in FIGS. 7 and 8, the samples of Examples 1 and 2 were confirmed to maintain their stent shapes without conspicuous signs of corrosion. On the other hand, as shown in FIG. 9, the sample of Comparative Example 1 was affected by much faster corrosion, and local fracture (local corrosion) was observed. These results revealed that the smooth surface was important in acquiring deformation followability. As shown in FIG. 10, in the sample of Comparative Example 2, corrosion throughout the whole surface (whole corrosion) was observed. Accordingly, it was suggested that the samples (Examples 1 and 2) which had elements based on the present invention exhibited the significant corrosion control effect compared with all the comparative samples (Comparative Examples 1 and 2) outside the scope of the present invention.

Change in Physical Properties of stent Before and After Immersion

The stent radial force of each of the samples before immersion as well as at 28 days after immersion in a simulated plasma solution was measured. Table 4 shows the result of the radial force residual ratio of the core structure before and after immersion calculated based on the radial force of the core structure before immersion. The radial force of the core structure before immersion was 63.12±5.36 N/mm

TABLE 4

Change in Physical Properties of Stent Sample Before and
After Immersion (Radial Force Residual Ratio [%])

|  | Before immersion | After immersion | Remarks |
|---|---|---|---|
| Ex. 1 | 100 | 92.8 ± 4.1 | FIG. 7 |
| Ex. 2 | 100 | 89.0 ± 5.8 | FIG. 8 |
| Com. Ex. 1 | 100 | 59.4 ± 9.4 | FIG. 9 |
| Com. Ex. 2 | 100 | 67.6 ± 5.0 | FIG. 10 |

Relative Evaluation of Stent at 28 Days After Immersion

The results revealed that the samples (Examples 1 and 2) with elements based on the present invention had radial force of 70% or higher at 28 days after immersion due to the corrosion control effect by the corrosion resistant layers. On the other hand, in the comparative samples (Comparative Examples 1 and 2) outside the scope of the present invention, accelerated corrosion resulted in significant deterioration in radial force. That is, in order to achieve the object of the present invention, it was confirmed that $MgF_2$ layer with corrosion resistance and deformation followability should be formed on the surface of the core structure. Details are described below.

Comparison with Comparative Example 1

As mentioned above, embodiments of the exemplary stents based on the present invention described in Examples 1 and 2, and comprise core structures of bioabsorbable magnesium alloy, with corrosion resistant layers of $MgF_2$ having a smooth surface (Ra) of 0.05 µm and a smooth surface (Ra) of 0.20 µm, respectively. On the other hand, a stent described in Comparative Example 1 comprises a corrosion resistant layer formed on the surface of the core structure; the corrosion resistant layer having a surface roughness (Ra: 0.30 µm) outside the present definition of the smooth surface. It was suggested that since the corrosion resistant layer formed in Comparative Example 1 did not have sufficient deformation followability, the corrosion resistant layer caused cracks by expansion in the simulated plasma solution and induced pitting corrosion (local corrosion). The results in Tables 3 and 4 confirmed that the weight residual ratios and the radial force residual ratios of Examples 1 and 2 were significantly higher than those in Comparative Example 1. Accordingly, the importance of forming the corrosion resistant layer having the smooth surface was confirmed in order to obtain the stent which had a capability to follow physical changes during diameter reduction and diameter expansion.

Comparison with Comparative Example 2

In Comparative Example 2, a bare core structure (Ra: 0.03 µm) without a corrosion resistant layer and with a smooth surface is shown. The weight residual ratios and radial force residual ratios in Examples 1 and 2 are significantly higher than those in Comparative Example 2. That is, it was suggested that formation of a corrosion resistant layer is indispensable in order to achieve a desired effect. The radial force residual ratio of Comparative Example 2 is significantly higher than that of Comparative Example 1 with a corrosion resistant layer. This suggests that there is a difference in corrosion mechanism between them. It is presumed that the stent of Comparative Example 1 falls into the accelerative pitting corrosion (local corrosion) starting from the crack occurred in the corrosion resistant layer during expansion, while the stent of Comparative Example 2 proceeds uniform corrosion (whole corrosion). Therefore, it is highly presumed that the corrosion resistant layer outside of the scope of the present invention (the corrosion resistant layer with a surface outside the definition on the smooth surface) adversely generates remarkable mechanical strength deterioration.

Change in Physical Properties of Stents in Pig Detention Tests

The recoil values of the stents at 28 days after detention in pig coronary arteries were measured. The results of the recoil values at 28 days after detention calculated based on the inner area (lumen area) of the stent before implant are shown in Table 5.

TABLE 5

Recoil Values of Inner Area (Lumen Area) of Stent Sample
at 28 Days After Detention in Pig

|  |  | Inner area (lumen area) of stent (mm$^2$) | | Recoil value (%) |
|---|---|---|---|---|
|  |  | Immediately after implant | 28 Days after implant |  |
| Example 1 | 1 | 7.22 ± 0.19 | 6.58 ± 0.31 | 7.05 ± 1.37 |
|  | 2 | 7.22 ± 0.31 | 6.82 ± 0.40 |  |
|  | 3 | 7.09 ± 0.27 | 6.61 ± 0.49 |  |
| Comparative Example 2 | 1 | 7.31 ± 0.36 | 5.87 ± 0.51 | 18.95 ± 2.21 |
|  | 2 | 7.15 ± 0.21 | 6.01 ± 0.32 |  |
|  | 3 | 7.26 ± 0.25 | 5.72 ± 0.21 |  |

Relative Evaluation at 28 Days After Detention of Stent in Pig

Immediately after implant of stents in pig coronary arteries, the status in which each of the stent samples of Example 1 and Comparative Example 2 was in contact to the vessel wall was confirmed. There is no significant difference in inner stent area between the samples. However, recoil value at 28 days after detention is 18.95±2.21% in Comparative Example 2 whereas 7.05±1.37% in Example 1 so that there is significant difference between samples. The large recoil value determined in Comparative Example 2 originates in an accelerative decline of the radial force accompanying complete corrosion. Thus, it was suggested that the sample (Example 1) with elements based on the present invention also achieves significant corrosion control effect in the pig coronary arteries compared with the comparative sample (Comparative Example 2) outside the scope of the present invention.

Water Contact Angle Determination

To the surface-treated disk sample (below-described Example 3 and Comparative Example 3), a waterdrop of 0.1 µL was dropped and the water contact angle on the sample surface was measured. DM-700 (Kyowa Interface Science, Inc) was used for water contact angle measurement.

Example 3

The disk sample (diameter of 5 mm and thickness of 1 mm) with an Ra of 0.05±0.01 µm was immersed in a 27 M hydrofluoric-acid aqueous solution (2 mL) and shaken at 100 rpm. After 24 hours the disk was taken out and fully washed ultrasonically with acetone aqueous solution, followed by dried at 60° C. for 24 hours under vacuum. A total of three samples were prepared on the same conditions as this condition.

Comparative Example 3

The disk sample (diameter of 5 mm and thickness of 1 mm) with an Ra of 0.05±0.01 μm was fully washed ultrasonically with acetone aqueous solution, followed by dried at 60° C. for 24 hours under vacuum. A total of three samples were prepared on the same conditions as this condition.

(Affinity Change of Disk Surface to Water)

Table 6 shows the results of water contact angles of the disk surfaces with smooth surface.

TABLE 6

Water Contact Angle of Disc Surface

|  | Corrosion resistant layer | Water contact angle (degree) |
|---|---|---|
| Example 3 | $MgF_2$ Ra: 0.05 μm | 10.3 ± 1.1 |
| Comparative Example 3 | None Ra: 0.05 μm | 52.1 ± 0.3 |

Relative Evaluation on Water Contact Angle

Figure 11A:
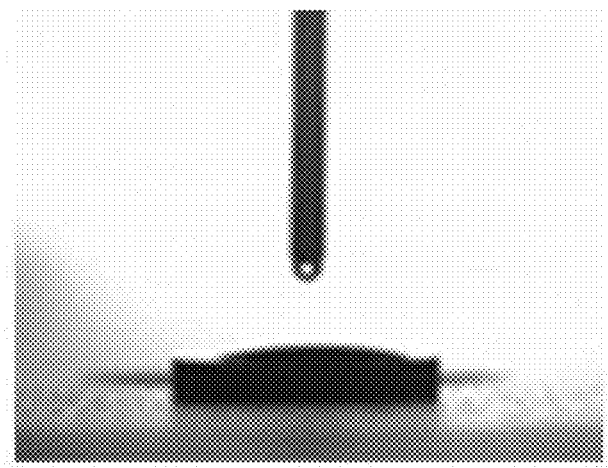
FIGS. 11A and 11B are images for water contact angle measurement of the disk which has a surface quality equivalent to the stent according to the present invention and that of Comparative Example, respectively.
Figure 11B:
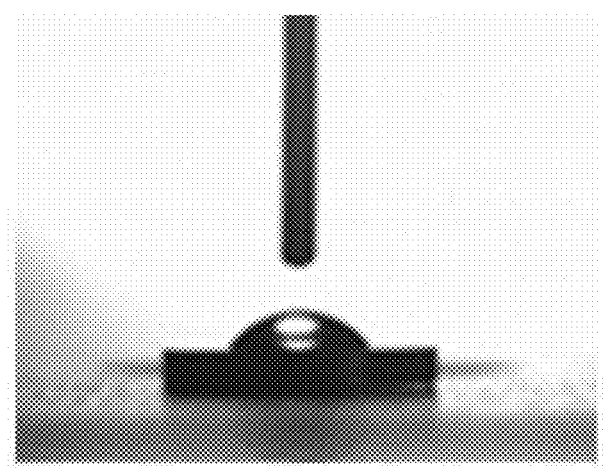

The water contact angle on the disk surface of Example 3 was 10.3±1.1 degrees (FIG. 11A), while that of Comparative Example 3 was 52.1±0.3 degrees (FIG. 11B), and there was significant difference between the samples. The results revealed that the surface of the sample (Example 3) which had elements based on the present invention was more hydrophilic than that of the comparative sample (Comparative Example 3) outside the scope of the present invention. It was suggested that the corrosion resistant layer formed by the fluoridation processing to the magnesium alloy with a smooth surface comprised $Mg(OH)_{2-x}F_x$.

Observation of Appearance Change of Polymer Coating

Each of the stent samples (below-described Example 4 and Comparative Example 4) coated with polymer was immersed in a 37° C. simulated plasma solution (EMEM+10% FBS) for 2 minutes, and then uniformly expanded until the sample had an inner diameter of 3 mm so as to observe the surface using SEM.

Example 4

Stent samples which were spray-coated with polycaprolactone (PCL) (200±20 μg per stent) containing sirolimus (100±10 μg per stent) were prepared.

Each of stent scaffolds having an Ra of 0.05±0.01 μm was immersed in a 27 M hydrofluoric-acid aqueous solution (2 mL) and reciprocally moved at a rate of 100 rpm. Then, the resultant stents taken out after 24 hours were subjected to ultrasonic cleaning with acetone aqueous solution sufficiently followed by drying them for 24 hours at 60° C. under vacuum (the procedure was the same as Example 1). Then, each of the stents was mounted on a mandrel of a coating apparatus at 9 mm below the nozzle and reciprocally moved at a rate of 120 rpm together with the mandrel. A 0.5% sirolimus/1% PCL coating solution in THF was applied for about 120 seconds at a spraying rate of 0.02 mL/min. to a surface of the stent ranging from one end thereof to an intermediate portion thereof so as to coat a half surface of the stent. Then, after drying the stent for 3 minutes at 60° C. under vacuum, the remaining half surface of the stent was coated. After crimping thus-obtained stent sample at the balloon catheter, ethylene oxide gas (EOG) sterilization was carried out to the prepared sample. A total of three samples were prepared on the same conditions as this condition.

Comparative Example 4

Stent samples which were spray-coated with polycaprolactone (PCL) (200±20 μg per stent) containing sirolimus (100±10 μg per stent) were prepared.

Each of stent scaffolds having an Ra of 0.05±0.01 μm was subjected to ultrasonic cleaning with acetone aqueous solution sufficiently followed by drying it for 24 hours at 60° C. under vacuum. (the procedure up to here was the same as in Comparative Example 2). Then, each of the stents was mounted on a mandrel of a coating apparatus at 9 mm below the nozzle and reciprocally moved at a rate of 120 rpm together with the mandrel. A 0.5% sirolimus/1% PCL coating solution in THF was applied for about 120 seconds at a spraying rate of 0.02 mL/min. to a surface of the stent ranging from one end thereof to an intermediate portion thereof so as to coat a half surface of the stent. Then, after drying the stent for 3 minutes at 60° C. under vacuum, the remaining half surface of the stent was coated. After crimping thus-obtained stent sample at the balloon catheter, ethylene oxide gas (EOG) sterilization was carried out to the prepared sample. A total of three samples were prepared on the same conditions as this condition.

Stent Surface Observation Immediately After Expansion

Figure 12A:
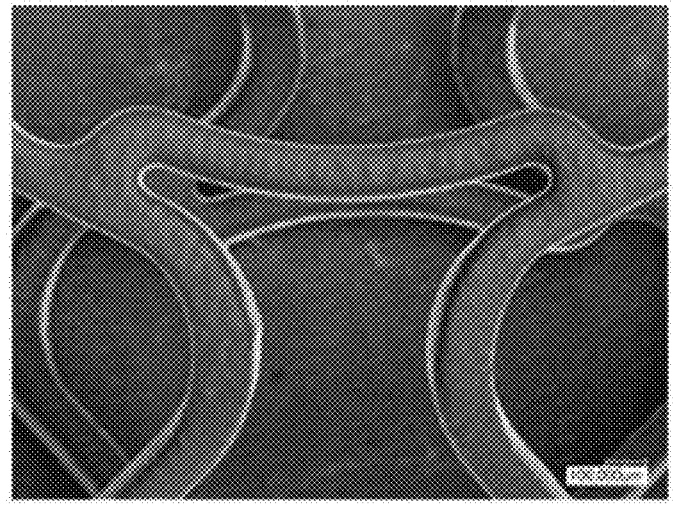
FIGS. 12A and 12B are SEM observation images showing an appearance change of the polymer coating surface of the stent according to the present invention and Comparative Example, respectively.
Figure 12B:
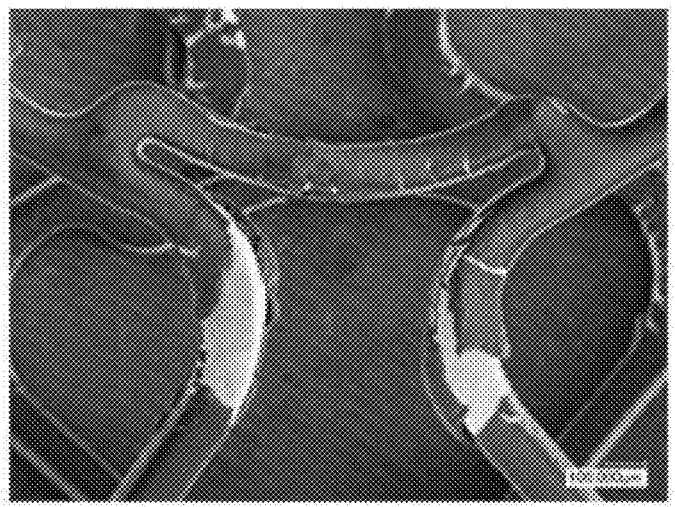

Serious damage (crack and exfoliation) was not recognized on the polymer coating surface (FIG. 12A) according to the sample (Example 4) having the elements based on the present invention after exposure to sequential the physical change caused by diameter reduction and diameter expansion. On the other hand, the crack and exfoliation were observed on the polymer coating surface (FIG. 12B) in comparative sample (Comparative Example 4) outside the scope of the present invention after expansion. Thus, it was suggested that the hydrophilic corrosion resistant layer formed on the magnesium alloy surface contributed to adhesive improvement with polymer.

INDUSTRIAL APPLICABILITY

Since the present invention provides a bioabsorbable stent which has a corrosion resistant layer effective in deterring accelerative corrosion of core structure accompanying a decline of mechanical strength of the stent, the present invention greatly contributes to medical technology development. Therefore, industrial applicability of the stent according to the present invention is extremely large.

Although the present invention has been fully described in connection with the preferred embodiments thereof with reference to the accompanying drawings, those skilled in the art will readily conceive numerous changes and modifications within the framework of obviousness upon the reading of the specification herein presented of the present invention.

Accordingly, such changes and modifications are to be construed as included therein.

REFERENCE NUMERALS

1 . . . A part of cell unit of a stent
2 . . . A part of cell unit of the stent in which diameter was reduced
3 . . . A part of cell unit of the stent in which diameter was expanded
4, 6, 8, 11, 14 . . . Core structure of Mg alloy 5, 7, 9, 12 . . . Corrosion resistant layer of $MgF_2$
10, 13 . . . Surface of corrosion resistant layer
15 . . . Surface of core structure
16, 19, 22 . . . Fluoridation processed stent sample
25 . . . Electrolytically polished Stent sample
17, 20, 23, 26 . . . Stent samples in which diameter reduction and diameter expansion were carried out
18, 21, 24, 27 . . . Stent sample at 28 days after simulated plasma solution immersion
28, 29 . . . Water-dropped disk sample
30, 31 . . . Polymer-coated stent sample

What is claimed is:

1. A bioabsorbable stent having a core structure, wherein the core structure comprises a magnesium (Mg) alloy, wherein the stent further comprises a corrosion resistant layer on the core structure,
wherein the magnesium alloy contains 93 mass % or more of Mg as a main component, 1.0 to 2.0 mass % of zinc (Zn), 0.05 to 0.80 mass % of zirconium (Zr), and 0.05 to 0.40 mass % of manganese (Mn) as accessory components, and 30 ppm or less of unavoidable impurities selected from the group consisting of iron (Fe), nickel (Ni), cobalt (Co), and copper (Cu), and the alloy excluding aluminum and at least one sort of rare earth material selected from the group consisting of scandium (Sc), yttrium (Y), dysprosium (Dy), Samarium (Sm), cerium (Ce), gadolinium (Gd), and lanthanum (La); and
wherein the corrosion resistant layer contains magnesium fluoride as a main component, and wherein the corrosion resistant layer has a hydrophilic smooth surface with a surface roughness (Ra) of 0.20 μm or less.

2. The bioabsorbable stent according to claim 1, wherein the magnesium alloy further contains 0.005 to 0.20 mass % of calcium (Ca).

3. The bioabsorbable stent according to claim 1, wherein one of the unavoidable impurities selected from the group consisting of Fe, Ni, Co, and Cu is contained at a proportion of less than 10 ppm in the magnesium alloy.

4. The bioabsorbable stent according to claim 1, wherein the hydrophilic smooth surface has a surface roughness of 0.10 μm or less.

5. The bioabsorbable stent according to claim 1, wherein a biodegradable polymer layer is formed on at least a part of the hydrophilic smooth surface of the corrosion resistant layer.

6. The bioabsorbable stent according to claim 5, wherein the stent is free from a gap between the corrosion resistant layer and the biodegradable polymer layer.

7. The bioabsorbable stent according to claim 5, wherein the biodegradable polymer layer contains an intimal thickening inhibitor.

8. The bioabsorbable stent according to claim 7, wherein the intimal thickening inhibitor is at least one member selected from the group consisting of sirolimus, everolimus, biolimus A9, zotarolimus, and paclitaxel.

9. A method of producing a bioabsorbable stent having a core structure comprising a magnesium alloy, the comprising:
forming a core structure comprising a magnesium alloy containing 93 mass % or more of Mg as a main component, 1.0 to 2.0 mass % of Zn, 0.05 to 0.80 mass % of Zr, and 0.05 to 0.40 mass % of Mn as accessory components, and 30 ppm or less of unavoidable impurities selected from the group consisting of Fe, Ni, Co, and Cu, and excluding aluminum and rare earth selected from the group consisting of Sc, Y, Dy, Sm, Ce, Gd, and La;
carrying out electrolytic polishing of the core structure; and
forming a corrosion resistant layer having a hydrophilic smooth surface with a surface roughness (Ra) of 0.2 μm or less which contains magnesium fluoride as a main component by fluoridation processing of the core structure surface.

10. The method of producing the bioabsorbable stent according to claim 9, wherein the electrolytic polishing is carried out until the core structure surface of comes to have a surface roughness (Ra) of 0.10 μm or less.

* * * * *